(12) United States Patent
Oishi et al.

(10) Patent No.: US 8,084,492 B2
(45) Date of Patent: Dec. 27, 2011

(54) BENZOFURAN COMPOUND AND PHARMACEUTICAL COMPOSITION CONTAINING THE SAME

(75) Inventors: Yoshitaka Oishi, Ashiya (JP); Takehiko Yokomizo, Fukuoka (JP)

(73) Assignee: The New Industry Research Organization, Hyogo (JP)

( * ) Notice: Subject to any disclaimer, the term of this patent is extended or adjusted under 35 U.S.C. 154(b) by 1207 days.

(21) Appl. No.: 11/791,026

(22) PCT Filed: Nov. 18, 2005

(86) PCT No.: PCT/JP2005/021630
§ 371 (c)(1),
(2), (4) Date: Jul. 6, 2007

(87) PCT Pub. No.: WO2006/054793
PCT Pub. Date: May 26, 2006

(65) Prior Publication Data
US 2009/0124687 A1    May 14, 2009

(30) Foreign Application Priority Data
Nov. 19, 2004    (JP) ................ 2004-335793

(51) Int. Cl.
*A61K 31/343* (2006.01)
*C07D 307/81* (2006.01)

(52) U.S. Cl. ...................... 514/469; 549/467

(58) Field of Classification Search ............ 514/469; 549/467
See application file for complete search history.

(56) References Cited

U.S. PATENT DOCUMENTS

| 4,610,983 | A | 9/1986 | Takagawa et al. |
| 4,745,127 | A * | 5/1988 | Atkinson et al. ............ 514/469 |
| 4,863,958 | A | 9/1989 | Belanger et al. |
| 5,296,495 | A | 3/1994 | Matsuo et al. |
| 6,143,762 | A | 11/2000 | Nash et al. |
| 6,362,210 | B1 | 3/2002 | Hauel et al. |
| 7,638,540 | B2 * | 12/2009 | Oishi et al. .................... 514/365 |
| 2004/0220191 | A1 | 11/2004 | Schwink et al. |
| 2005/0187261 | A1 | 8/2005 | Verner et al. |
| 2006/0194851 | A1 | 8/2006 | Oishi et al. |

FOREIGN PATENT DOCUMENTS

| JP | 60-138539 | 7/1985 |
| WO | 99/21856 | 5/1999 |
| WO | 00/06153 | 2/2000 |

OTHER PUBLICATIONS

Theodora Vokoglou-Nomikos et al. (CLinical Cancer Research, vol. 9, 4227-4239, Sep. 15, 2003).*
Alain Aurozo et al., "*Synthesis and Pharmacological properties of benzofurans substituted in the 2 position by an acidic group*", European Journal of Medicinal Chemistry, vol. 10, No. 2, pp. 182-186 (1975).
Foo Pan et al., "*Studies of Benzofurans as Potential Antimicrobial Agents. II. Synthesis of β-(2-Benzofuryl)-Acrylic Acid and Its Derivatives*", Journal of the Chinese Chemical Society, vol. 1961, No. 8 (Ser. II), pp. 374-379 (1962).
Paul D. Greenspan et al., "*Carboxy-Substituted Cinnamides: A Novel Series of Potent, Orally Active $LTB_4$ Receptor Antagonists*", Journal of Medicinal Chemistry, vol. 42, No. 1, pp. 164-172 (1999).

* cited by examiner

*Primary Examiner* — Sabiha Qazi
(74) *Attorney, Agent, or Firm* — Wenderoth, Lind & Ponack, L.L.P.

(57) ABSTRACT

The present invention relates to a compound having a leukotriene (particularly leukotriene B4) inhibitory action, and useful for the prophylaxis or treatment of diseases such as allergy, asthma, inflammation, cancer and the like.

6 Claims, No Drawings

BENZOFURAN COMPOUND AND PHARMACEUTICAL COMPOSITION CONTAINING THE SAME

TECHNICAL FIELD

The present invention relates to a benzofuran compound having a leukotriene (particularly leukotriene B4) inhibitory activity, a pharmaceutically acceptable salt thereof and prodrugs thereof. Moreover, the present invention relates to a pharmaceutical composition comprising the benzofuran compound or a pharmaceutically acceptable salt thereof or a prodrug thereof. Furthermore, the present invention relates to a leukotriene inhibitor, a BLT2-competitive inhibitor, an agent for the prophylaxis or treatment of allergy, an agent for the prophylaxis or treatment of asthma, an agent for the prophylaxis or treatment of inflammation, an agent for the prophylaxis or treatment of cancer, and the like, which comprise the above-mentioned benzofuran compound or a pharmaceutically acceptable salt thereof or a prodrug thereof.

BACKGROUND ART

Leukotriene B4 (LTB4) is one kind of arachidonic acid metabolites and one of the most potent activation substances of neutrophil and macrophage (see e.g., Samuelsson et al., "science", (1987), vol. 237, pp. 1171-1176 and Shimizu et al., "Journal of Neurochemistry", (1990), vol. 55, pp. 1-15). It is known that action of LTB4 on neutrophil or macrophage results in the induction of various responses important for biological defense, such as adhesion to vascular endothelial cells, degranulation of lysosome enzymes, production of active oxygen, chemotaxis into inflammatory tissues and the like. However, overproduction of LTB4 is deeply involved in the formation and aggravation of various diseases accompanied by inflammations or allergic responses, such as psoriasis (see e.g., Iversen et al., "Skin Pharmacology", (1997), vol. 10, pp. 169-177), bronchial asthma (see e.g., Turner et al., "The Journal of Clinical Investigation", (1996), vol. 97, pp. 381-387), rheumatoid arthritis (see e.g., Griffiths et al., "Proceedings of the National Academy of Science of the USA", (1995), vol. 92, pp. 517-521), inflammatory bowel disease (see e.g., Sharon et al., "Gastroenterology", (1984), vol. 86, pp. 453-460), ischemic renal failure (see e.g., Noiri et al., "Proceedings of the National Academy of Science of the USA", (2000), vol. 97, pp. 823-828) and the like.

Therefore, the development of a therapeutic agent capable of selectively inhibiting the production or action of LTB4 in various ways has been desired for the prophylaxis or treatment of these diseases. In recent years, it has been clarified that LTB4 receptors include two kinds of receptors (BLT1, BLT2) having different expression distributions and affinities (see e.g., Yokomizo et al., "Nature", (1997), vol. 387, pp. 620-624 and Yokomizo et al., "The Journal of the Experimental Medicine", (2000), vol. 192, pp. 421-431). Therefore, expansion of the scope of LTB4 inhibitor selection has been desired more than ever.

For example, it has been reported that LTB4 receptor antagonists are useful for the treatment of patients with chronic rheumatoid arthritis (e.g., Alten et al., Annals of the Rheumatic Diseases, 2004, vol. 63, pp. 170-176). However, which of the two kinds of LTB4 receptors (BLT1, BLT2) the antagonist mainly acts on, and which receptor is mainly involved in chronic rheumatoid arthritis are not described.

Moreover, it is suggested that LTB4 stimulates the growth of cancer cells besides the above-mentioned diseases, and a report has documented that LTB4 receptor antagonists inhibited the growth of human pancreatic cancer, and induced the apoptosis of cancer cells (e.g., Tong et al., Clinical Cancer Research, 2002, vol. 8, pp. 3232-3242). However, which of the two kinds of LTB4 receptors (BLT1, BLT2) the antagonist mainly acts on, and which receptor is mainly involved in the growth of cancer are not described.

On the other hand, while benzofuran derivatives having a leukotriene inhibitory action have been disclosed (e.g., JP-A-61-17579, JP-A-5-202040 and JP-A-5-317024), the selectivity to LTB4 has not been disclosed.

DISCLOSURE OF THE INVENTION

An object of the present invention is to provide a highly safe compound having a strong leukotriene (particularly leukotriene B4) inhibitory action, particularly BLT2 competitive inhibitory action, whereby conferring variety to a leukotriene inhibitor, a BLT2 competitive inhibitor, an agent for the prophylaxis or treatment of allergy, an agent for the prophylaxis or treatment of asthma, an agent for the prophylaxis or treatment of inflammation, an agent for the prophylaxis or treatment of cancer to expand the scope of selection.

An object of the present invention is to increase diversity of and broaden the selection range of leukotriene inhibitors, BLT2 competitive inhibitors, agents for the prophylaxis or treatment of allergy, agents for the prophylaxis or treatment of asthma and agents for the prophylaxis or treatment of inflammation, by providing compounds having a potent leukotriene (particularly leukotriene B4) inhibitory action and a BLT2 competitive inhibitory action as well as high safety.

The present inventors have conducted intensive studies in an attempt to solve the above-mentioned problems and found that a compound having a benzofuran structure, a pharmaceutically acceptable salt thereof, and prodrugs thereof have a strong leukotriene (particularly leukotriene B4) inhibitory action, are particularly superior in a BLT2 competitive inhibitory action and a BLT2 blocking action, and have high safety, which resulted in the completion of the present invention.

Accordingly, the present invention relates to the following.

[1] A compound represented by the formula (IA)

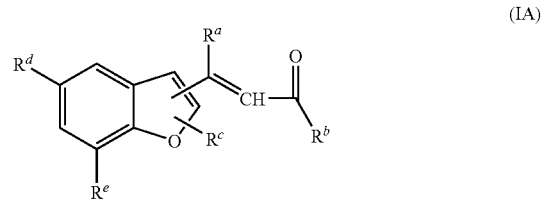

wherein $R^a$ is a hydrogen atom, a $C_{1-6}$ alkyl group, or an optionally substituted $C_{6-14}$ aryl group;
$R^b$ is an optionally substituted amino group;
$R^c$ is a hydrogen atom, a $C_{1-6}$ alkyl group, or an optionally substituted $C_{6-14}$ aryl group;
$R^d$ is a hydrogen atom, a halogen atom, or a nitro group; and
$R^e$ is a hydrogen atom, or —O—$R^4$, wherein $R^4$ is a hydrogen atom or a $C_{1-6}$ alkyl group [the alkyl group is optionally substituted by one or more substituents selected from the group consisting of a halogen atom, —COOAlk, an amino group (the amino group is optionally mono- or di-substituted by a $C_{1-6}$ alkyl group), a sulfanyl group, a $C_{6-14}$ arylsulfanyl group (aryl of the arylsulfanyl group is optionally substituted by one or more halogen atoms) and a $C_{6-14}$ aryl group (the aryl group is optionally substituted by one or more substituents selected from the group consisting of a hydroxyl group and a $C_{1-6}$ alkoxy group)],
or a pharmaceutically acceptable salt thereof, or a prodrug thereof.

[2] A compound represented by the formula (I)

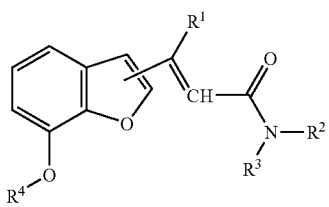

(I)

wherein $R^1$ is a hydrogen atom or a $C_{1-6}$ alkyl group;
$R^2$ and $R^3$ are the same or different and each is a hydrogen atom or a $C_{1-6}$ alkyl group (the alkyl group is optionally substituted by one or more —COOAlk);
$R^4$ is a hydrogen atom or a $C_{1-6}$ alkyl group [the alkyl group is optionally substituted by one or more substituents selected from the group consisting of a halogen atom, —COOAlk, an amino group (the amino group is optionally mono- or di-substituted by a $C_{1-6}$ alkyl group), a sulfanyl group, a $C_{6-14}$ arylsulfanyl group (aryl of the arylsulfanyl group is optionally substituted by one or more halogen atoms) and a $C_{6-14}$ aryl group (the aryl group is optionally substituted by one or more substituents selected from the group consisting of a hydroxyl group and a $C_{1-6}$ alkoxy group), or a pharmaceutically acceptable salt thereof, or a prodrug thereof.

[3] The compound of [1] or [2], which is (E)-3-[7-(1-phenylethoxy)-benzofuran-2-yl]-but-2-enoic acid diethylamide or a pharmaceutically acceptable salt thereof, or a prodrug thereof.

[4] A pharmaceutical composition comprising the compound of any one of [1]-[3] or a pharmaceutically acceptable salt thereof, or a prodrug thereof, and a pharmaceutically acceptable carrier.

[5] The pharmaceutical composition of [4], which is a leukotriene inhibitor.

[6] The pharmaceutical composition of [4], which is a BLT2 competitive inhibitor.

[7] The pharmaceutical composition of [4], which is an agent for the prophylaxis or treatment of allergy.

[8] The pharmaceutical composition of [4], which is an agent for the prophylaxis or treatment of asthma.

[9] The pharmaceutical composition of [4], which is an agent for the prophylaxis or treatment of inflammation.

[10] The pharmaceutical composition of [4], which is an agent for the prophylaxis or treatment of cancer.

[A] A method of inhibiting leukotriene, which comprises administering an effective amount of the above-mentioned compound or a pharmaceutically acceptable salt thereof, or a prodrug thereof to a mammal.

[B] Use of the above-mentioned compound or a pharmaceutically acceptable salt thereof, or a prodrug thereof for the production of a leukotriene inhibitor.

[C] Use of the above-mentioned compound or a pharmaceutically acceptable salt thereof, or a prodrug thereof for the production of an agent for the prophylaxis or treatment of allergy.

[D] Use of the above-mentioned compound or a pharmaceutically acceptable salt thereof, or a prodrug thereof for the production of an agent for the prophylaxis or treatment of asthma.

[E] Use of the above-mentioned compound or a pharmaceutically acceptable salt thereof, or a prodrug thereof for the production of an agent for the prophylaxis or treatment of inflammation.

The benzofuran compound of the present invention and a pharmaceutically acceptable salt thereof, and prodrugs thereof have superior leukotriene inhibitory action, BLT2 competitive inhibitory action, BLT2 blocking action, prophylactic or therapeutic action on allergy, prophylactic or therapeutic action on asthma, prophylactic or therapeutic action on inflammation, prophylactic or therapeutic action on cancer and the like and are useful as agents for the prophylaxis or treatment of diseases such as allergic disease, asthma, inflammation, cancer and the like, and other diseases.

BEST MODE OF EMBODIMENT OF THE INVENTION

The present invention provides a benzofuran compound represented by the following formula (IA), having a leukotriene (particularly leukotriene B4) inhibitory action, and a pharmaceutically acceptable salt thereof, and prodrugs thereof:

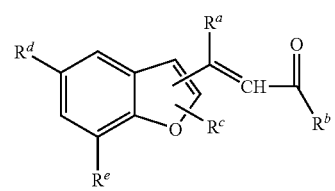

(IA)

wherein $R^a$ is a hydrogen atom, a $C_{1-6}$ alkyl group, or an optionally substituted $C_{6-14}$ aryl group;
$R^b$ is an optionally substituted amino group;
$R^c$ is a hydrogen atom, a $C_{1-6}$ alkyl group, or an optionally substituted $C_{6-14}$ aryl group;
$R^d$ is a hydrogen atom, a halogen atom, or a nitro group; and
$R^e$ is a hydrogen atom, or —O—$R^4$,
wherein $R^4$ is a hydrogen atom or an optionally substituted $C_{1-6}$ alkyl group.

In one preferable embodiment, the present invention provides a benzofuran compound represented by the following formula (I) having a leukotriene (particularly leukotriene B4) inhibitory action, a pharmaceutically acceptable salt thereof, and prodrugs thereof:

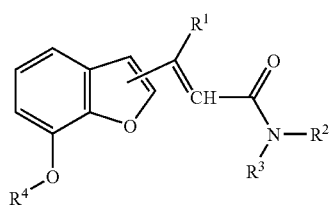

(I)

wherein $R^1$ is a hydrogen atom or a $C_{1-6}$ alkyl group;
$R^2$ and $R^3$ are the same or different and each is a hydrogen atom or a $C_{1-6}$ alkyl group (the alkyl group is optionally substituted by one or more —COOAlk);
$R^4$ is a hydrogen atom or a $C_{1-6}$ alkyl group [the alkyl group is optionally substituted by one or more substituents selected from the group consisting of a halogen atom, —COOAlk, an amino group (the amino group is optionally mono- or di-substituted by a $C_{1-6}$ alkyl group), a sulfanyl group, a $C_{6-14}$ arylsulfanyl group (aryl of the arylsulfanyl group is optionally substituted by one or more halogen atoms) and a $C_{6-14}$ aryl group (the aryl group is optionally substituted by one or more substituents selected from the group consisting of a hydroxyl group and a $C_{1-6}$ alkoxy group).

The leukotriene inhibitory action in the present invention includes, for example, an action to inhibit binding of leukotriene to leukotriene receptor (e.g., competitive inhibitory action etc.), an action to inhibit production of leukotriene, an action to inhibit leukotriene metabolism, an action to inhibit reaction caused by the action of leukotriene and the like. The leukotriene inhibitory action preferably is an action to inhibit binding of leukotriene to leukotriene receptor, an action to inhibit reaction caused by the action of leukotriene and the like, more preferably an action to inhibit binding of leukotriene to leukotriene receptor.

In addition, the inhibitory action may be any of an inhibitory action in a molecule unit, an inhibitory action in a cell unit, an inhibitory action in a tissue unit and an inhibitory action in an individual unit.

Leukotriene in the present invention includes, for example, leukotriene A4 (LTA4), leukotriene B4 (LTB4), leukotriene C4 (LTC4), leukotriene D4 (LTD4), metabolites thereof and the like, and includes any compound capable of binding to a leukotriene receptor (leukotriene receptor ligand). Leukotriene is preferably leukotriene B4.

As the leukotriene B4 receptor, BLT1, BLT2 and the like can be mentioned, which are free of any particular limitation. Leukotriene B4 receptor is preferably BLT2.

That is, the compound of the present invention is superior in the action of inhibiting binding of LTB4 to BLT2 (BLT2 competitive inhibitory action) or inhibiting reactions caused by the action of LTB4 via BLT2 (BLT2 blocking action).

That the above-mentioned BLT2 competitive inhibitory action is BLT2 specific means that the action of inhibiting binding of LTB4 to BLT2 is stronger than the action of inhibiting LTB4 from binding to other LTB4 receptor (e.g., BLT1).

That the BLT2 blocking action is BLT2 specific means that the action of inhibiting reactions caused by the action of LTB4 via BLT2 is stronger than the action of inhibiting reactions caused by the action via other LTB4 receptor (e.g., BLT1).

Each symbol used in the present description is explained in the following.

When used in the present specification, unless otherwise specified, the halogen atom means a fluorine atom, a chlorine atom, a bromine atom or an iodine atom.

When used in the present specification, unless otherwise specified, the "$C_{1-6}$ alkyl group" means, for example, methyl, ethyl, propyl, isopropyl, butyl, isobutyl, sec-butyl, tert-butyl, pentyl, isopentyl, neopentyl, hexyl and the like.

When used in the present specification, unless otherwise specified, the "Alk" of "—COOAlk" means a hydrogen atom or a $C_{1-6}$ alkyl group.

When used in the present specification, unless otherwise specified, the "$C_{6-14}$ aryl group" means, for example, phenyl, naphthyl, anthryl, phenanthryl, acenaphthylenyl, biphenylyl and the like.

When used in the present specification, unless otherwise specified, the "$C_{1-6}$ alkoxy group" means, for example, methoxy, ethoxy, propoxy, isopropoxy, butoxy, isobutoxy, sec-butoxy, pentyloxy, hexyloxy and the like.

As the $C_{1-6}$ alkyl group for $R^a$, methyl is preferable.

As the "$C_{6-14}$ aryl group" of the "optionally substituted $C_{6-14}$ aryl group" for $R^a$, phenyl is preferable. In addition, the "optionally substituted $C_{6-14}$ aryl group" for $R^a$ optionally has 1 to 5, the same or different substituent selected from, for example, (1) halogen atom;
(2) $C_{1-6}$ alkyl group;
(3) hydroxy group;
(4) $C_{1-6}$ alkoxy group;
(5) hydroxy-$C_{1-6}$ alkyl group;
(6) $C_{1-6}$ alkyl-carbonyl group;
(7) carboxy group;
(8) $C_{1-6}$ alkoxy-carbonyl group;
(9) cyano group;
(10) carbamoyl group;
(11) sulfamoyl group;
(12) nitro group;
(13) amino group;
(14) $C_{1-6}$ alkyl-carbonylamino group;
(15) $C_{1-6}$ alkoxy-carbonylamino group; and
(16) $C_{1-6}$ alkylsulfonylamino group at substitutable position(s).

As the "optionally substituted $C_{6-14}$ aryl group" for $R^a$, a phenyl group optionally substituted by 1 or 2 substituents selected from a halogen atom (preferably chlorine atom) and a $C_{1-6}$ alkoxy group (preferably methoxy group) is preferable.

The "optionally substituted amino group" for $R^b$ optionally has 1 or 2 substituents at substitutable position(s).

As such substituent, for example, (1) $C_{1-6}$ alkyl group optionally substituted by one or more —COOAlk;
(2) optionally substituted $C_{6-14}$ aryl group; and
(3) optionally substituted $C_{6-14}$ aryl-$C_{1-6}$ alkyl group can be mentioned. When two substituents are possessed, the substituents may be the same or different.

As preferable —COOAlk of the above-mentioned "$C_{1-6}$ alkyl group optionally substituted by one or more —COOAlk", —COOH, —COOCH$_3$, —COOC$_2$H$_5$ and the like can be mentioned, and more preferably —COOC$_2$H$_5$. The number of the substituent is preferably 0 or 1. The number of the substituent of 0 means that a $C_{1-6}$ alkyl group is unsubstituted.

The "optionally substituted $C_{6-14}$ aryl" of the above-mentioned substituent or in the substituents is as defined for the "optionally substituted $C_{6-14}$ aryl group" for $R^a$.

As the "optionally substituted amino group" for $R^b$, amino group optionally substituted by substituent selected from a $C_{1-4}$ alkyl group, an optionally substituted phenyl group, and an optionally substituted phenyl-$C_{1-4}$ alkyl group is preferable. Furthermore, as the "$C_{1-4}$ alkyl group", methyl group or ethyl group is preferable, and as the "optionally substituted phenyl group", a phenyl group optionally substituted by one or two $C_{1-6}$ alkoxy groups (more preferably, methoxy group) is preferable.

When the nitrogen atom constituting the above-mentioned amino group is substituted by two substituents, these substituents may form a nitrogen-containing heterocycle together with the adjacent nitrogen atom. As the "nitrogen-containing heterocycle", for example, a 3- to 8-membered, nitrogen-containing heterocycle containing, as a ring-constituting atom, at least one nitrogen atom besides carbon atom, and one or two hetero atoms selected from oxygen atom, sulfur atom and nitrogen atom can be mentioned. As preferable examples of the nitrogen-containing heterocycle, 5- or 6-membered cyclic amino (e.g., 1-pyrrolidinyl group, piperidinyl, 1-piperazinyl, morpholinyl) optionally containing an oxygen atom can be mentioned.

In the formula (IA), $R^c$ is a group substitutable at the 2-position or 3-position of the benzofuran ring.

The "optionally substituted $C_{6-14}$ aryl group" for $R^c$ is as defined for the "optionally substituted $C_{6-14}$ aryl group" for $R^a$, and is preferably a phenyl group.

As the halogen atom for $R^d$, a chlorine atom or a bromine atom is preferable.

The definition of $R^4$ when $R^e$ is —O—$R^4$ is as mentioned below.

The $C_{1-6}$ alkyl group for $R^1$ is, for example, methyl, ethyl, propyl, isopropyl, butyl, isobutyl, sec-butyl, tert-butyl, pentyl, isopentyl, neopentyl, hexyl and the like, preferably methyl or ethyl, and more preferably methyl.

The $C_{1-6}$ alkyl group for $R^2$ or $R^3$ is, for example, methyl, ethyl, propyl, isopropyl, butyl, isobutyl, sec-butyl, tert-butyl, pentyl, isopentyl, neopentyl, hexyl and the like, preferably methyl, ethyl, propyl or isopropyl, and more preferably ethyl.

The above-mentioned $C_{1-6}$ alkyl group may be substituted by one or more —COOAlk. Preferable —COOAlk includes —COOH, —COOCH$_3$, —COOC$_2$H$_5$ and the like, more preferably —COOC$_2$H$_5$. The number of the substituent is preferably 0 or 1. The number of the substituent of 0 means that $R^2$ and $R^3$ are unsubstituted $C_{1-6}$ alkyl groups.

The $C_{1-6}$ alkyl group for $R^4$ includes, for example, methyl, ethyl, propyl, isopropyl, butyl, isobutyl, sec-butyl, tert-butyl, pentyl, isopentyl, neopentyl, hexyl and the like, preferably methyl, ethyl, propyl and isopropyl.

The alkyl group is optionally substituted by one or more substituents selected from the group consisting of a halogen atom, —COOAlk, an amino group, a sulfanyl group, a $C_{6-14}$ arylsulfanyl group and a $C_{6-14}$ aryl group. The halogen atom that may substitute the alkyl group includes, for example, a fluorine atom, a chlorine atom, a bromine atom and an iodine atom. The halogen atom is preferably a chlorine atom.

Examples of preferable —COOAlk that may substitute the alkyl group include —COOH, —COOCH$_3$, —COOC$_2$H$_5$ and the like.

The amino group that may substitute the alkyl group is optionally mono- or di-substituted by a $C_{1-6}$ alkyl group. The $C_{1-6}$ alkyl group that may substitute the amino group includes, for example, methyl, ethyl, propyl, isopropyl, butyl, isobutyl, sec-butyl, tert-butyl, pentyl, isopentyl, neopentyl, hexyl and the like, preferably methyl and ethyl. For example, the amino group is preferably —NH$_2$, —NH(CH$_3$), —N(CH$_3$)$_2$, —N(C$_2$H$_5$)$_2$ and the like.

The $C_{6-14}$ aryl moiety of the $C_{6-14}$ arylsulfanyl group that may substitute the $C_{1-6}$ alkyl group for $R^4$ is, for example, phenyl, naphthyl and the like, preferably phenyl. The aryl is optionally substituted by one or more halogen atoms. The halogen atom is, for example, a fluorine atom, a chlorine atom, a bromine atom, an iodine atom and the like, preferably a chlorine atom. While the number of halogen atom that substitutes the aryl is not particularly limited, it is, for example, 0-3, preferably 0 or 1. As used herein, the number of the substituent of 0 means that the $C_{6-14}$ aryl moiety of the $C_{6-14}$ arylsulfanyl group that may substitute the $C_{1-6}$ alkyl group for $R^4$ is unsubstituted.

The $C_{6-14}$ aryl group that may substitute the $C_{1-6}$ alkyl group for $R^4$ is, for example, phenyl, naphthyl and the like, preferably phenyl. The aforementioned $C_{6-14}$ aryl group may be substituted by one or more substituents selected from the group consisting of a hydroxyl group and a $C_{1-6}$ alkoxy group. The aforementioned $C_{1-6}$ alkoxy group is a linear or branched chain alkoxy group, which may contain one oxygen such as methoxy, ethoxy and propoxy, or two oxygens such as methylenedioxy. The $C_{1-6}$ alkoxy group is preferably methoxy. The number of the substituent for the aryl group is, for example, 0-3, preferably 0 or 1.

As used herein, the number of the substituent of 0 means that the aforementioned $C_{6-14}$ aryl group is unsubstituted. The number of the substituent for the $C_{1-6}$ alkyl group for $R^4$ is, for example, 0-3, preferably 0-2.

As used herein, the number of the substituent of 0 means that $R^1$ is an unsubstituted alkyl group.

The benzofuran compound of the present invention has a substituent of the following formula:

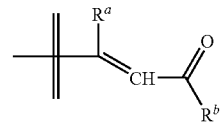

wherein each symbol is as defined above, at the 2-position or 3-position of the benzofuran ring in the above-mentioned formula (IA), preferably at the 2-position of the benzofuran ring.

In one preferable embodiment, the benzofuran compound of the present invention has a substituent of the following formula:

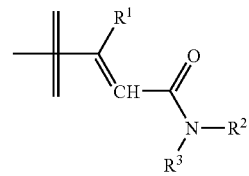

wherein $R^1$ is as defined above, more preferably, $R^1$ is methyl, $R^2$ and $R^3$ are as defined above, more preferably, $R^2$ and $R^3$ are ethyl, at the 2-position or 3-position of the benzofuran ring in the above-mentioned formula (IA), preferably at the 2-position of the benzofuran ring. The other symbols in the formula (I) are as defined above.

The carbon-carbon double bond at the 2-position or 3-position of the benzofuran ring forms a conjugated triene system together with two double bonds contained in the above-mentioned substituents.

The conjugated triene system contains, unlike normal conjugated triene systems of carbon-carbon double bond, a semi-unsaturated double bond of amide bond. Therefore, it is preferable for achieving a potent leukotriene inhibitory activity, or strong BLT2 competitive inhibitory activity and/or BLT2 blocking action.

Specific examples of preferable benzofuran compound, a pharmaceutically acceptable salt thereof, and prodrugs thereof of the present invention include (E)-3-[7-(1-phenylethoxy)-benzofuran-2-yl]-but-2-enoic acid diethylamide having the following structure,

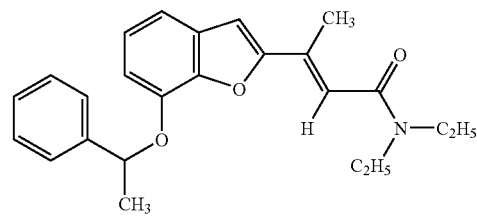

a pharmaceutically acceptable salt thereof and prodrugs thereof.

While steric isomers (cis form and trans form or Z form and E form) are present due to the double bond in the above-mentioned substituents at the 2-position or 3-position of the benzofuran ring in the formulas (IA) and (I), all isomers are encompassed in the present invention.

In addition, when stereoisomers (cis form and trans form or Z form and E form) are present due to the double bond in the compound of the present invention, all of such isomers are encompassed in the present invention, unless otherwise specified.

The benzofuran compounds of the present invention represented by the formulas (IA) and (I) (to be also referred to as "the benzofuran compound of the present invention" or "the compound of the present invention" in the present specification) may form a pharmaceutically acceptable salt. When the benzofuran compound of the present invention has a basic group, it can form an acid addition salt. The acid to be used for forming such an acid addition salt is not particularly limited as long as it can form a salt with a basic moiety and is pharmaceutically acceptable. As such acid, inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like can be mentioned.

When the benzofuran compound of the present invention has an acidic group such as carboxyl group and the like, it can form, for example, alkali metal salts (e.g., sodium salt, potassium salt and the like), alkaline earth metal salts (e.g., calcium salt, magnesium salt and the like) or organic base salts (e.g., triethylamine salt, dicyclohexylamine salt, pyridine salt, tert-butylamine salt and the like).

The compound or a pharmaceutically acceptable salt thereof of the present invention may be used as a prodrug. Such prodrug refers to a compound which is converted to the compound of the present invention by a reaction due to an enzyme, an gastric acid, etc. under the physiological conditions in the living body, that is, a compound which is converted to the compound of the present invention by enzymatic oxidation, reduction, hydrolysis, etc., or a compound which is converted to the compound of the present invention by hydrolysis etc. due to gastric acid, etc.

The prodrug of the compound of the present invention includes a compound obtained by subjecting an amino group in the compound of the present invention to an acylation, alkylation or phosphorylation (e.g., a compound obtained by subjecting an amino group in the compound of the present invention to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in the compound of the present invention to an acylation, alkylation, phosphorylation or boration (e.g., a compound obtained by subjecting an hydroxy group in the compound of the present invention to an acetylation, palmitoylation, propanoylation, pivaloylation, succinylation, fumarylation, alanylation, dimethylaminomethylcarbonylation, etc.); a compound obtained by subjecting a carboxyl group in the compound of the present invention to an esterification or amidation (e.g., a compound obtained by subjecting a carboxyl group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like.

Any of these compounds can be produced from the compound of the present invention by a method known per se. In addition, the prodrug of the compound of the present invention may also be one which is converted to the compound of the present invention under physiological conditions, such as those described in IYAKUHIN no KAIHATSU (Development of Pharmaceuticals), Vol. 7, Design of Molecules, p. 163-198, Published by HIROKAWA SHOTEN (1990).

The compound of the present invention may be labeled with an isotope (e.g., $^3$H, $^{14}$C, $^{35}$S, $^{125}$I and the like) and the like.

The compound of the present invention can be produced by organic synthesis methods known in the field.

As specific examples, the benzofuran compound (I) of the present invention can be produced from the compound (compound (II)) of the formula (II)

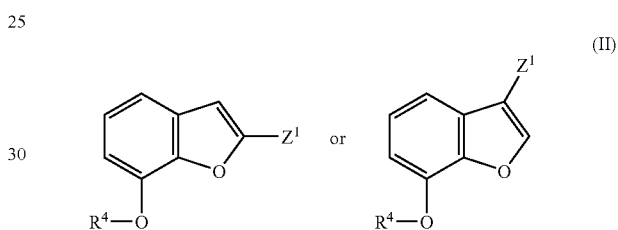

wherein $Z^1$ is a halogen atom, or

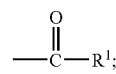

and $R^1$ and $R^4$ are as defined above, and the like by any of the following production methods, or a method according to the methods.

In the formula (II), the halogen atom for $Z^1$ is, for example, a fluorine atom, a chlorine atom, a bromine atom, an iodine atom and the like, preferably a bromine atom.

(Production Method 1)

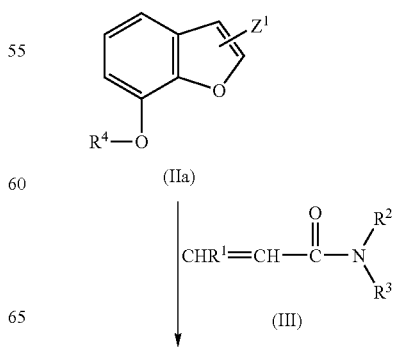

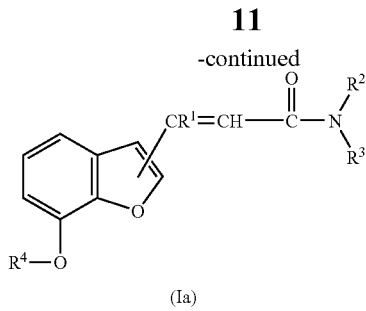

(Ia)

In the formulas, $R^1$, $R^2$, $R^3$ and $R^4$ are as defined above, $Z^1$ is a halogen atom (a fluorine atom, a chlorine atom, a bromine atom, an iodine atom etc.).

Production Method 1 is a method for producing a compound of the formula (Ia) (compound (Ia)) by reacting a compound of the formula (IIa) (compound (IIa)), which is a compound of the formula (II) wherein $Z^1$ is a halogen atom, with a compound of the formula (III) (compound (III)).

This production method is generally performed by conducting a reaction exemplified by the Heck reaction (Organic Reactions, vol. 27, p. 345, 1982). The reaction is generally carried out in the presence of a solvent palladium catalyst.

The solvent to be used for Production Method 1 is not particularly limited as long as it does not inhibit the reaction. For example, triethylamine, acetonitrile, dimethylformamide (DMF) and the like; and mixtures thereof and the like can be mentioned as the solvent.

The amount of compound (III) to be used for Production Method 1 is not particularly limited, and it is generally, 1-5 mol, preferably 1-3 mol, per 1 mol of compound (IIa).

As the palladium catalyst for Production Method 1, for example, palladium acetate, palladium carbon, palladium alumina, palladium zeolite, palladium silica, palladium oxide and the like can be mentioned. The amount of the catalyst to be used is generally 0.001-0.5 mol, preferably 0.001-0.1 mol, per 1 mol of compound (IIa).

In Production Method 1, a phosphine ligand may be added to maintain the catalyst activity. As the phosphine ligand, for example, tri-o-tolylphosphine and the like can be mentioned. The amount of the phosphine ligand to be used is generally 1-5 mol, preferably 1-3 mol, per 1 mol of the palladium catalyst.

While the reaction conditions for Production Method 1 such as reaction temperature, reaction time and the like vary depending on the reaction reagent, reaction solvent and the like, they are generally −30° C. to 150° C. and 30 min to 24 hr. Where necessary, a sealed tube may be used and the reaction may be carried out in a closed system.

The compound (IIa) can be produced by any of the following methods.

(Production Method a-1)

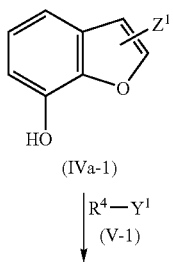

(IVa-1)

$\downarrow$ $R^4$—$Y^1$
(V-1)

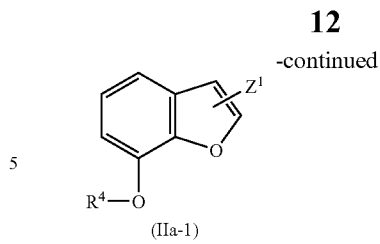

(IIa-1)

In the formulas, $R^4$ is as defined above, $Y^1$ and $Z^1$ are halogen atoms (fluorine atom, chlorine atom, bromine atom, iodine atom etc.).

The reaction of Production Method a-1 is generally carried out in a solvent in the presence of a base.

The solvent to be used in Production Method a-1 is not particularly limited as long as it does not inhibit the reaction. For example, acetone, dioxane, acetonitrile, tetrahydrofuran, chloroform, methylene chloride, ethylene chloride, benzene, toluene, xylene, ethyl acetate, N,N-dimethylformamide, dimethyl sulfoxide and the like; and mixtures thereof and the like can be mentioned as the solvent.

While the base to be used in Production Method a-1 is not particularly limited, inorganic bases such as alkali metal carbonates (e.g., sodium carbonate, sodium hydrogencarbonate, potassium carbonate, potassium hydrogen carbonate and the like), alkali metal hydroxide salts (e.g., sodium hydroxide, potassium hydroxide and the like), metal hydride compounds (e.g., sodium hydride, potassium hydride, calcium hydride and the like) and the like; and organic bases such as alkali metal alkoxides (e.g., sodium methoxide, sodium ethoxide, potassium-t-butoxide and the like), amines (e.g., triethylamine, diisopropylethylamine and the like) and the like can be mentioned.

While the amount of compound (V-1) to be used in Production Method a-1 is not particularly limited, it is generally 1-5 mol, preferably 1-3 mol, per 1 mol of compound (IVa-1).

While the reaction conditions in Production Method a-1 such as reaction temperature, reaction time and the like vary depending on the reaction reagent, reaction solvent and the like to be used, they are generally −30° C. to 150° C. and 30 min to 24 hr.

In addition, the compound (IVa-1) can be produced by the method shown in Production Method b.

(Production Method b)

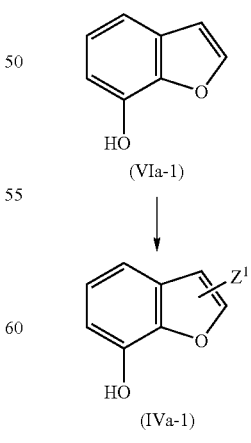

In the formula, $Z^1$ is a halogen atom (fluorine atom, chlorine atom, bromine atom, iodine atom etc.).

In Production Method b, compound (IVa-1) can be produced by halogenizing the benzofuran ring of compound (VIa-1) at a substitutable position (e.g., 2-position or 3-position) by a method known per se.

(Production Method 2)

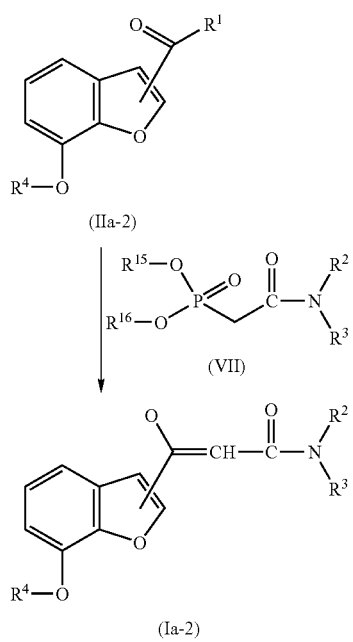

In the formulas, $R^1$, $R^2$, $R^3$ and $R^4$ are as defined above, and $R^{15}$ and $R^{16}$ are the same or different and each is a $C_{1-6}$ alkyl group, a $C_{6-14}$ aryl group and the like.

Production Method 2 is a method for producing a compound of the formula (Ia-2) (compound (Ia-2)) by reacting a compound of the formula (IIa-2) (compound (IIa-2)), which is a compound of the formula (II), wherein $Z^1$ is

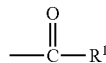

with a compound of the formula (VII) (compound (VII)).

This production method can be generally performed by conducting a reaction exemplified by the Wittig-Horner-Emmons reaction (Chemistry Review, vol. 74, p. 87 (1974)). The reaction is generally carried out in a solvent.

The solvent to be used in Production Method 2 is not particularly limited as long as it does not inhibit the reaction. For example, dioxane, acetonitrile, tetrahydrofuran, chloroform, methylene chloride, ethylene chloride, benzene, toluene, xylene, ethyl acetate, dimethyl sulfoxide and the like; a mixture thereof and the like can be mentioned as the solvent.

While the amount of compound (VII) to be used in Production Method 2 is not particularly limited, it is generally 1-5 mol, preferably 1-3 mol, per 1 mol of compound (IIa-2).

While the reaction conditions in Production Method 2 such as reaction temperature, reaction time and the like vary depending on the reaction reagent, reaction solvent and the like to be used, they are generally −30° C. to 150° C. and 30 min to 24 hr.

The compound (IIa-2) can be produced according to (Production Method a-1) in (Production Method 1).

The benzofuran compound (I) obtained in the above-mentioned Production Method can be isolated by a conventional method and purified as necessary by, for example, recrystallization, preparative thin layer chromatography, column chromatography and the like.

In addition, a compound represented by the formula (IA) (benzofuran compound (IA)) can be produced by a method according to the production method of the above-mentioned benzofuran compound (I).

The benzofuran compound (I) and benzofuran compound (IA) can be converted to a pharmaceutically acceptable salt thereof by a method known per se.

A pharmaceutical composition comprising the compound of the present invention or a pharmaceutically acceptable salt thereof or a prodrug thereof can contain additive and the like. As the additive, for example, excipients (e.g., starch, gum arabic, carboxymethylcellulose, hydroxypropylcellulose, crystalline cellulose and the like), lubricants (e.g., magnesium stearate, talc and the like), disintegrants (e.g., carboxymethylcellulose calcium, talc and the like) and the like can be mentioned.

After mixing with the above-mentioned various components, the mixture can be processed to give, for example, a preparation for oral administration such as capsule, tablet, fine granules, granules, dry syrup and the like or a preparation for parenteral administration such as injection, suppository and the like by a method known per se.

While the dose of the compound of the present invention or a pharmaceutically acceptable salt thereof or a prodrug thereof varies depending on the subject of administration, symptoms and other factors, a dose of about 0.01-500 mg is administered 1-3 times a day for oral administration to an adult patient with, for example, allergy, asthma, inflammation or cancer.

The compound of the present invention, a pharmaceutically acceptable salt thereof and prodrugs thereof show superior leukotriene inhibitory action, BLT2 competitive inhibitory action, BLT2 blocking action, prophylactic or therapeutic action on allergy, prophylactic or therapeutic action on asthma, prophylactic or therapeutic action on inflammation, prophylactic or therapeutic action on cancer and the like for mammals (human, horse, bovine, dog, cat, rat, mouse, hamster and the like), and are useful for the prophylaxis or treatment of allergic diseases (e.g., allergic dermatitis, allergic rhinitis and the like), atopic dermatitis, asthma, chronic obstructive pulmonary disease (COPD), inflammation, inflammatory eye disease, inflammatory pulmonary diseases (e.g., chronic pneumonia, silicosis, pulmonary sarcoidosis, pulmonary tuberculosis and the like), arthritis (e.g., chronic rheumatoid arthritis, osteoarthritis, rheumatoid spondylitis, gouty arthritis, synovitis and the like), inflammatory bowel diseases (e.g., Crohn's disease, ulcerative colitis and the like), psoriasis, rheumatism, meningitis, hepatitis, ischemic renal failure, nephritis, Addison's disease, systemic lupus erythematosus, osteoporosis, toxemia, cachexia, central nervous disorders (e.g., cerebrovascular disorders such as cerebral hemorrhage, cerebral infarction etc., head trauma, spinal trauma, brain edema and the like), arteriosclerosis, cancer and/or tumor in the head, neck, eyeball, mouth, throat, esophagus, chest, bone, lung, colon, rectal, stomach, prostate, breast, ovary, kidney, liver, pancreas, brain and the like, prophylaxis or treatment of leukotriene-related diseases, and prophylaxis or treatment of BLT2-related diseases, and the like.

The present invention is explained in detail in the following by referring to Examples, which are mere examples of the present invention and should not be construed as limitative.

EXAMPLES

Example 1

Synthesis of (E)-3-[7-(1-phenylethoxy)-benzofuran-2-yl]-but-2-enoic acid-diethylamide

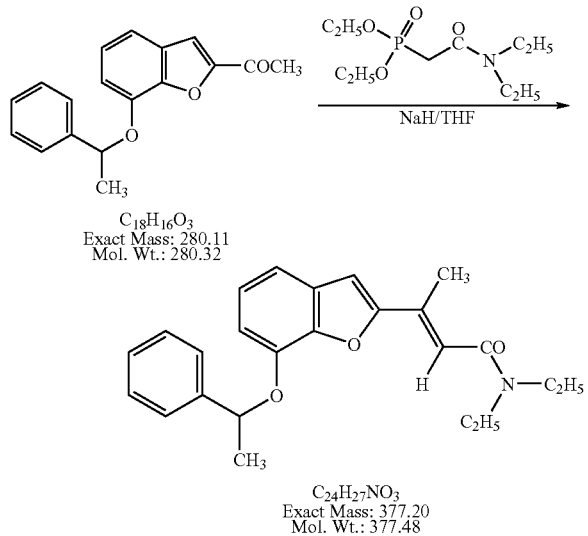

While replacing with nitrogen, NaH (0.13 g, 0.0054 mol) was suspended in absolute THF (20 mL), and N,N-diethylphosphonoacetamide (1.36 g, 0.0054 mol)/absolute THF (10 mL) was added dropwise at 0° C. Then, 2-acetyl-7-(1-phenylethoxy)benzo[b]furan (1.0 g, 0.0036 mol)/absolute THF (20 mL) was added dropwise. After stirring for 6 h while allowing to warm to room temperature, the disappearance of the starting materials was confirmed by TLC. The reaction mixture was poured into saturated aqueous NH$_4$Cl solution, mixed and THF was evaporated under reduced pressure. The residue was extracted with ethyl acetate, washed with brine, dried over absolute magnesium sulfate, and evaporated under reduced pressure to give a pale-yellow oil. The obtained oil was purified by column chromatography to give the title compound as a pale-yellow oil. (0.75 g, 55.6%)

Rf=0.46 (CHCl$_3$:AcOEt=20:1)

$^1$H-NMR(CHCl$_3$, 500 MHz)

δ1.20-1.27 (6H, m, NCH$_2$CH$_3$×2), δ1.72 (3H, d, OCHCH$_3$, J=6.5 Hz), δ2.31 (3H, d, C(CH$_3$)=CH, J=0.9 Hz), δ3.43-3.51 (4H, m, NCH$_2$CH$_3$×2), δ5.58 (1H, q, OCHCH$_3$, J=6.4 Hz), δ6.74 (1H, dd, 4-H or 6-H, J=8.2 and 1.1 Hz), δ6.91 (1H, d, C(CH$_3$)=CH, J=0.9 Hz), δ6.99 (1H, dd, 5-H, J=7.7 Hz), δ7.10 (1H, dd, 4-H or 6-H, J=7.8 and 1.4 Hz), δ7.23-7.45 (5H, m, phenyl-H).

EIMS (70 eV)m/z (rel., int., %) 377 (M$^+$, 10.29), 273(100), 201 (61.41)

HREIMS m/z 377.1992 (calcd for C$_{24}$H$_{27}$NO$_3$ 377.1991)

The compounds shown in the following Table A were synthesized by a method according to Example 1.

TABLE A

| Ex. No. | Structural formula | Molecular formula | M. W. | m. p. (° C.) |
|---|---|---|---|---|
| 2 | (H$_3$CO, H$_3$CO-phenyl-ethyl-NH-OC-C=C(CH$_3$)-benzofuran(Cl, CH$_3$), Z-form) | C$_{23}$H$_{24}$ClNO$_4$ | 413.89 | 150.9-151.5 |
| 3 | (OCH$_3$, OCH$_3$-phenyl-ethyl-HN-CO-C=C(CH$_3$)-benzofuran(Cl, CH$_3$)) | C$_{23}$H$_{24}$ClNO$_4$ | 413.89 | 73.0-76.0 |

TABLE A-continued

| Ex. No. | Structural formula | Molecular formula | M. W. | m. p. (° C.) |
|---|---|---|---|---|
| 4 | | $C_{20}H_{18}ClNO_3$ | 355.81 | 139.0-142.0 |
| 5 | | $C_{23}H_{24}BrNO_4$ | 458.34 | 143.1-150.0 |
| 6 | | $C_{21}H_{19}BrClNO_2$ | 432.74 | 106.7-109.8 |
| 7 | | $C_{22}H_{20}ClNO_3$ | 381.85 | oil<br>Rf = 0.14 (CHCl$_3$:AcOEt = 20:1)<br>H$^1$-NMR (CD$_3$Cl$_3$, 500 MHz)<br>δ 2.34 (3 H, d, J = 0.9, —CCH$_3$=CH)<br>δ 3.46-3.72 (8 H, m, morpholine-H)<br>δ 6.23 (1 H, d, J = 1.4, —C=CH)<br>δ 7.28 (1 H, dd, J = 8.7, J = 1.9, BF-6H)<br>δ 7.39-7.46 (4 H, m, BF-7H, Phe-H)<br>δ 7.51 (1 H, d, J = 2.3, BF-4H)<br>δ 7.77-7.79 (2 H, m, Phe-H)<br>EIMS (70eV) m/z (rel. int, %): 381 (M$^+$, 65.82), 295 (100.00), 267 (39.59)<br>HREZMS m/z 381.1131 (calcd for C$_{22}$H$_{20}$NO$_3$Cl 381.1132) |

TABLE A-continued

| Ex. No. | Structural formula | Molecular formula | M. W. | m. p. (° C.) |
|---|---|---|---|---|
| 8 | | $C_{15}H_{17}NO_2$ | 243.3 | oil<br>Rf = 0.16 (CHCl₃:AcOEt = 20:1)<br>H¹-NMR (CD₃Cl₃, 400 MHz)<br>δ 1.21-1.34 (6 H, m, —CH₂CH₃)<br>δ 3.52 (4 H, q, J = 14.3, —CH₂CH₃)<br>δ 6.96 (1 H, d, J = 15.4, CH=CH)<br>δ 7.32-7.37 (2 H, m, BF-5, 6 H)<br>δ 7.53 (1 H, dd, J = 6.9, J = 21.8, BF-7H)<br>δ 7.78 (1 H, dd, J = 6.6, J = 1.8, BF-4H)<br>δ 7.81 (1 H, d, J = 15.3, CH=CH)<br>δ 7.85 (1 H, s, BF-3H)<br>EIMS (70eV) m/z (rel. int, %):<br>243 (M⁺, 63.71),<br>171 (100.00), 143 (6.44)<br>HREZMS m/z 243.1260 (calcd for $C_{22}H_{22}ClNO_2$ 243.1259) |
| 9 | | $C_{21}H_{21}NO_4$ | 351.4 | 138.1-140.3 |
| 10 | | $C_{21}H_{17}BrClNO_3$ | 446.72 | 150.0-153.5 |
| 11 | | $C_{28}H_{26}ClNO_4$ | 475.96 | 169.1-171.9 |

TABLE A-continued

| Ex. No. | Structural formula | Molecular formula | M. W. | m. p. (° C.) |
| --- | --- | --- | --- | --- |
| 12 | (5-chloro-2-phenylbenzofuran-3-yl with CH₃C=CH-C(O)N(C₂H₅)₂ substituent) | $C_{22}H_{22}ClNO_2$ | 367.87 | oil<br>E/Z mixture<br>Rf = 0.39 (CHCl₃:AcOEt = 20:1)<br>H¹-NMR (CD₃Cl₃, 400 MHz)<br>δ 1.16 (3H, t, J = 7.2, —CH₂CH₃)<br>δ 1.22 (3H, t, J = 7.2, —CH₂CH₃)<br>δ 2.31 (1 H, d, J = 1.5, CH₃C=CH)<br>δ 3.36 (2 H, q, J = 14.3, —CH₂CH₃)<br>δ 3.49 (2 H, q, J = 14.3, —CH₂CH₃)<br>δ 6.28 (1 H, q, J = 2.8, CH₃C=CH)<br>δ 7.27 (1 H, dd, J = 8.6, J = 2.2, BF-6H)<br>δ 7.32-7.47 (4 H, m, BF-7H, Phe-H)<br>δ 7.53 (1 H, d, J = 1.9, BF-4H)<br>δ 7.79-7.82 (2 H, m, Phe-H)<br>EIMS (70eV) m/z (rel. int, %): 367 (M⁺, 73.03), 295 (100.00), 267 (32.50), 232 (32.11)<br>HREZMS m/z 369.1309 (calcd for $C_{22}H_{22}ClNO_2$ 367.1339) |
| 13 | (5-bromobenzofuran-2-yl with C(=CH-C(O)N(C₂H₅)₂)-(4-methoxyphenyl) substituent) | $C_{22}H_{22}BrNO_3$ | 428.32 | 93.5-96.0 |
| 14 | (benzofuran-3-yl-CH=CH-C(O)-morpholine) | $C_{15}H_{15}NO_3$ | 257.28 | 132.1-134.6 |

TABLE A-continued
| Ex. No. | Structural formula | Molecular formula | M. W. | m. p. (° C.) |
| --- | --- | --- | --- | --- |
| 15 | 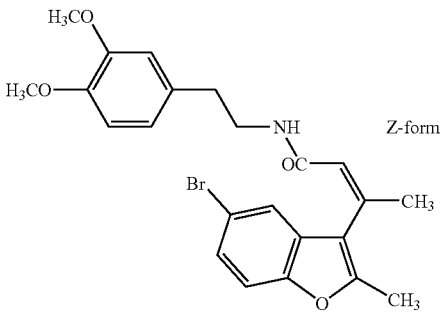 Z-form | $C_{23}H_{24}BrNO_4$ | 458.34 | 150.1-153.5 |
| 16 | 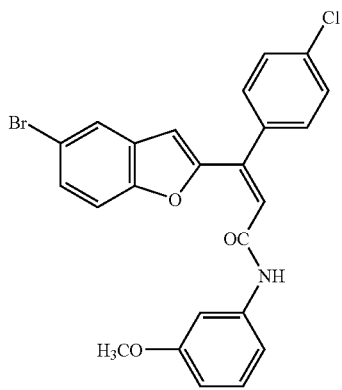 | $C_{24}H_{17}BrClNO_3$ | 482.75 | 160.1-162.2 |
| 17 | 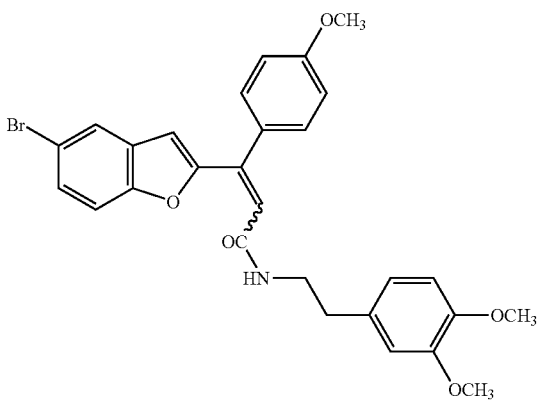 | $C_{28}H_{26}BrNO_5$ | 536.41 | 112.2-117.0 E/Z mixture |
| 18 | 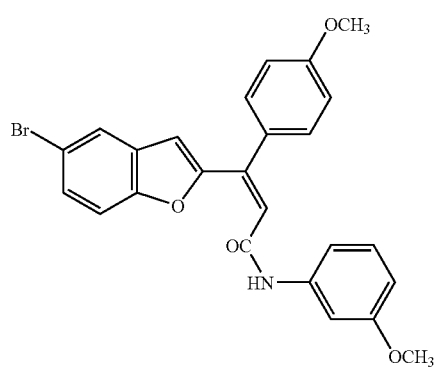 | $C_{25}H_2OBrNO_4$ | 478.33 | 136.4-138.5 |

TABLE A-continued

| Ex. No. | Structural formula | Molecular formula | M. W. | m. p. (° C.) |
|---|---|---|---|---|
| 19 | (structure shown) | $C_{22}H_2OBrNO_4$ | 442.3 | 158.2-160.1 |
| 20 | (structure shown) | $C_{17}H_{20}N_2O_4$ | 316.35 | 130.0-134.0 |
| 21 | (structure shown) | $C_{23}H_{24}N_2O_6$ | 424.45 | 116.9-124.4 E/Z mixture |

Experimental Example 1

CHO cells harbouring a gene encoding human BLT1 or human BLT2 and functionally expressing the receptor were seeded in a 96 well plate at $4\times10^4$ cells/well, and cultured at 37° C. for 60 min. The culture supernatant was removed and a loading buffer (100 µl) containing 4 µM Fluo-3 (manufactured by Dojindo), 0.04% pluoronic acid (manufactured by Sigma) and 1% serum was added. The cells were cultured at 37° C. for 30 min to introduce Fluo-3 into the cells. After culture, the cells were washed with a buffer, and a buffer containing the compound of Example 1 (10 µM (final concentration)) was added, and then 100 nM (final concentration) of leukotriene B4 (LTB4) was added. Changes in the intracellular calcium ion concentration were measured with Flex-station (manufactured by Molecular Devices Corporation) as an increase in the fluorescence intensity (area under a curve in a time-course graph of fluorescence intensity in 10 min measurement). As a positive control of BLT1 and BLT2 antagonists, ZK158252, a known LTB4 inhibitor, was used.

Increase in the intracellular calcium ion concentration of the CHO cells harbouring BLT1 or BLT2 due to LTB4 stimulation was significantly suppressed by ZK158252 to a similar level.

Increase in the intracellular calcium ion concentration of the CHO cells harbouring BLT2 was suppressed by the compound of Example 1 at an intensity equivalent to or greater than the suppression by ZK158252. On the other hand, the suppressive effect of the compound of Example 1 on the increase in the intracellular calcium ion concentration of the CHO cells harbouring BLT1 due to the LTB4 stimulation was weaker as compared to the effect on BLT2.

From the foregoing results, it is suggested that the compound of the present invention has a superior leukotriene B4 inhibitory action. Moreover, since the compound of the present invention showed a suppressive effect more specific to BLT2 rather than BLT1, its superior BLT2 competitive inhibitory activity was demonstrated.

INDUSTRIAL APPLICABILITY

The benzofuran compound of the present invention and a pharmaceutically acceptable salt thereof, and prodrugs thereof have superior leukotriene inhibitory action, BLT2 competitive inhibitory action, BLT2 blocking action, prophylactic or therapeutic action on allergy, prophylactic or therapeutic action on asthma, prophylactic or therapeutic action on inflammation, prophylactic or therapeutic action on cancer and the like and are useful as agents for the prophylaxis or treatment of diseases such as allergic disease, asthma, inflammation, cancer and the like, and other diseases.

This application is based on application No. 2004-335793 filed in Japan, the contents of which are incorporated hereinto by reference.

The invention claimed is:

1. A compound represented by the formula (I)

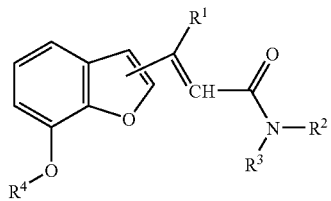

(I)

wherein $R^1$ is a $C_{1-6}$ alkyl group;
$R^2$ and $R^3$ are the same or different and each is a $C_{1-6}$ alkyl group, wherein the alkyl group is optionally substituted by one or more —COOAlk;
$R^4$ is a $C_{1-6}$ alkyl group, wherein the alkyl group is optionally substituted by one or more substituents selected from the group consisting of a halogen atom, —COOAlk, an amino group, wherein the amino group is optionally mono- or di-substituted by a $C_{1-6}$ alkyl group, a sulfanyl group, a $C_{6-14}$ arylsulfanyl group, wherein aryl of the arylsulfanyl group is optionally substituted by one or more halogen atoms and a $C_{6-14}$ aryl group, wherein the aryl group is optionally substituted by one or more substituents selected from the group consisting of a hydroxyl group and a $C_{1-6}$ alkoxy group,
or a pharmaceutically acceptable salt thereof.

2. The compound of claim 1, which is (E)-3-[7-(1-phenylethoxy)-benzofuran-2-yl]-but-2-enoic acid diethylamide or a pharmaceutically acceptable salt thereof.

3. A pharmaceutical composition comprising the compound of claim 1 or a pharmaceutically acceptable salt thereof, and a pharmaceutically acceptable carrier.

4. A method of treating an allergy in a mammal, comprising administrating a therapeutically effective amount of the compound of claim 1 or a pharmaceutically acceptable salt thereof to the mammal.

5. A method of treating asthma in a mammal, comprising administrating a therapeutically effective amount of the compound of claim 1 or a pharmaceutically acceptable salt thereof to the mammal.

6. A method of treating inflammation in a mammal, comprising administrating a therapeutically effective amount of the compound of claim 1 or a pharmaceutically acceptable salt thereof to the mammal.

* * * * *